United States Patent
Kaleta

(10) Patent No.: US 11,672,654 B2
(45) Date of Patent: Jun. 13, 2023

(54) ALTERNATE STENT CAF DESIGN FOR TAVR

(71) Applicant: St. Jude Medical, Cardiology Division, Inc., St. Paul, MN (US)

(72) Inventor: Richard Kaleta, Arden Hills, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 41 days.

(21) Appl. No.: 16/933,324

(22) Filed: Jul. 20, 2020

(65) Prior Publication Data

US 2021/0030536 A1 Feb. 4, 2021

Related U.S. Application Data

(60) Provisional application No. 62/880,758, filed on Jul. 31, 2019.

(51) Int. Cl.
*A61F 2/24* (2006.01)

(52) U.S. Cl.
CPC .......... *A61F 2/2418* (2013.01); *A61F 2/2409* (2013.01); *A61F 2210/0014* (2013.01)

(58) Field of Classification Search
CPC ........ A61F 2/2409; A61F 2/2418; A61F 2/24; A61F 2210/0014; A61F 2220/0075; A61F 2250/0036; A61F 2/2415; A61F 2/2412
See application file for complete search history.

(56) References Cited

U.S. PATENT DOCUMENTS

| | | | |
|---|---|---|---|
| 3,657,744 A | 4/1972 | Ersek | |
| 4,275,469 A | 6/1981 | Gabbay | |
| 4,491,986 A | 1/1985 | Gabbay | |
| 4,759,758 A | 7/1988 | Gabbay | |
| 4,878,906 A | 11/1989 | Lindemann et al. | |
| 4,922,905 A | 5/1990 | Strecker | |
| 4,994,077 A | 2/1991 | Dobben | |
| 5,411,552 A | 5/1995 | Andersen et al. | |

(Continued)

FOREIGN PATENT DOCUMENTS

| | | |
|---|---|---|
| DE | 19857887 A1 | 7/2000 |
| DE | 10121210 B4 | 11/2005 |

(Continued)

OTHER PUBLICATIONS

International Search Report for Application No. PCT/US2020/042776 dated Oct. 16, 2020, 2 pages.

(Continued)

*Primary Examiner* — Yashita Sharma

(74) *Attorney, Agent, or Firm* — Wei & Sleman LLP

(57) ABSTRACT

A prosthetic heart valve includes a stent extending in a longitudinal direction and having a collapsed condition and an expanded condition. The stent includes a plurality of struts forming cells and a plurality of commissure attachment features spaced apart in an annular direction of the stent and extending in a medial direction of the stent. A valve assembly is secured to the commissure attachment features, the valve assembly including a cuff and a plurality of leaflets, each of the leaflets having a free edge and being capable of alternating between an open position and a closed position. A method of manufacturing the prosthetic heart valve is also provided.

13 Claims, 6 Drawing Sheets

(56) References Cited

U.S. PATENT DOCUMENTS

| | | | |
|---|---|---|---|
| 5,415,664 | A | 5/1995 | Pinchuk |
| 5,480,423 | A | 1/1996 | Ravenscroft et al. |
| 5,843,167 | A | 12/1998 | Dwyer et al. |
| 5,855,601 | A | 1/1999 | Bessler et al. |
| 5,910,170 | A | 6/1999 | Reimink et al. |
| 5,935,163 | A | 8/1999 | Gabbay |
| 5,961,549 | A | 10/1999 | Nguyen et al. |
| 6,077,297 | A | 6/2000 | Robinson et al. |
| 6,083,257 | A | 7/2000 | Taylor et al. |
| 6,090,140 | A | 7/2000 | Gabbay |
| 6,214,036 | B1 | 4/2001 | Letendre et al. |
| 6,264,691 | B1 | 7/2001 | Gabbay |
| 6,267,783 | B1 | 7/2001 | Letendre et al. |
| 6,368,348 | B1 | 4/2002 | Gabbay |
| 6,419,695 | B1 | 7/2002 | Gabbay |
| 6,454,799 | B1 * | 9/2002 | Schreck ............... A61F 2/2436 623/2.14 |
| 6,458,153 | B1 | 10/2002 | Bailey et al. |
| 6,468,660 | B2 | 10/2002 | Ogle et al. |
| 6,488,702 | B1 | 12/2002 | Besselink |
| 6,517,576 | B2 | 2/2003 | Gabbay |
| 6,533,810 | B2 | 3/2003 | Hankh et al. |
| 6,582,464 | B2 | 6/2003 | Gabbay |
| 6,610,088 | B1 | 8/2003 | Gabbay |
| 6,623,518 | B2 | 9/2003 | Thompson et al. |
| 6,685,625 | B2 | 2/2004 | Gabbay |
| 6,719,789 | B2 | 4/2004 | Cox |
| 6,730,118 | B2 | 5/2004 | Spenser et al. |
| 6,783,556 | B1 | 8/2004 | Gabbay |
| 6,790,230 | B2 | 9/2004 | Beyersdorf et al. |
| 6,814,746 | B2 | 11/2004 | Thompson et al. |
| 6,830,584 | B1 | 12/2004 | Seguin |
| 6,869,444 | B2 | 3/2005 | Gabbay |
| 6,893,460 | B2 | 5/2005 | Spenser et al. |
| 6,908,481 | B2 | 6/2005 | Cribier |
| 7,018,406 | B2 | 3/2006 | Seguin et al. |
| 7,025,780 | B2 | 4/2006 | Gabbay |
| 7,137,184 | B2 | 11/2006 | Schreck |
| 7,160,322 | B2 | 1/2007 | Gabbay |
| 7,247,167 | B2 | 7/2007 | Gabbay |
| 7,267,686 | B2 | 9/2007 | DiMatteo et al. |
| 7,311,730 | B2 | 12/2007 | Gabbay |
| 7,374,573 | B2 | 5/2008 | Gabbay |
| 7,381,218 | B2 | 6/2008 | Schreck |
| 7,452,371 | B2 | 11/2008 | Pavcnik et al. |
| 7,510,572 | B2 | 3/2009 | Gabbay |
| 7,524,331 | B2 | 4/2009 | Birdsall |
| RE40,816 | E | 6/2009 | Taylor et al. |
| 7,585,321 | B2 | 9/2009 | Cribier |
| 7,682,390 | B2 | 3/2010 | Seguin |
| 7,731,742 | B2 | 6/2010 | Schlick et al. |
| 7,803,185 | B2 | 9/2010 | Gabbay |
| 7,846,203 | B2 | 12/2010 | Cribier |
| 7,846,204 | B2 | 12/2010 | Letac et al. |
| 7,857,845 | B2 | 12/2010 | Stacchino et al. |
| 7,914,569 | B2 | 3/2011 | Nguyen et al. |
| D648,854 | S | 11/2011 | Braido |
| D652,926 | S | 1/2012 | Braido |
| D652,927 | S | 1/2012 | Braido et al. |
| D653,341 | S | 1/2012 | Braido et al. |
| D653,342 | S | 1/2012 | Braido et al. |
| D653,343 | S | 1/2012 | Ness et al. |
| D654,169 | S | 2/2012 | Braido |
| D654,170 | S | 2/2012 | Braido et al. |
| D660,432 | S | 5/2012 | Braido |
| D660,433 | S | 5/2012 | Braido et al. |
| D660,967 | S | 5/2012 | Braido et al. |
| D684,692 | S | 6/2013 | Braido |
| 8,840,661 | B2 | 9/2014 | Manasse |
| 8,840,663 | B2 | 9/2014 | Salahieh et al. |
| 9,700,442 | B2 * | 7/2017 | White ..................... A61F 2/24 |
| 10,004,597 | B2 * | 6/2018 | Li ........................ A61F 2/2418 |
| 11,020,221 | B2 * | 6/2021 | Arcaro .................... A61F 2/24 |
| 2002/0036220 | A1 | 3/2002 | Gabbay |
| 2003/0023303 | A1 | 1/2003 | Palmaz et al. |
| 2003/0050694 | A1 | 3/2003 | Yang et al. |
| 2003/0130726 | A1 | 7/2003 | Thorpe et al. |
| 2004/0049262 | A1 | 3/2004 | Obermiller et al. |
| 2004/0093075 | A1 | 5/2004 | Kuehne |
| 2004/0210304 | A1 | 10/2004 | Seguin et al. |
| 2005/0096726 | A1 | 5/2005 | Sequin et al. |
| 2005/0137695 | A1 | 6/2005 | Salahieh et al. |
| 2005/0137697 | A1 | 6/2005 | Salahieh et al. |
| 2005/0240200 | A1 | 10/2005 | Bergheim |
| 2005/0256566 | A1 | 11/2005 | Gabbay |
| 2006/0008497 | A1 | 1/2006 | Gabbay |
| 2006/0074484 | A1 | 4/2006 | Huber |
| 2006/0122692 | A1 | 6/2006 | Gilad et al. |
| 2006/0149360 | A1 | 7/2006 | Schwammenthal et al. |
| 2006/0173532 | A1 | 8/2006 | Flagle et al. |
| 2006/0178740 | A1 | 8/2006 | Stacchino et al. |
| 2006/0195180 | A1 | 8/2006 | Kheradvar et al. |
| 2006/0206202 | A1 | 9/2006 | Bonhoeffer et al. |
| 2006/0241744 | A1 | 10/2006 | Beith |
| 2006/0241745 | A1 | 10/2006 | Solem |
| 2006/0259120 | A1 | 11/2006 | Vongphakdy et al. |
| 2006/0259137 | A1 | 11/2006 | Artof et al. |
| 2006/0265056 | A1 | 11/2006 | Nguyen et al. |
| 2006/0276813 | A1 | 12/2006 | Greenberg |
| 2007/0010876 | A1 | 1/2007 | Salahieh et al. |
| 2007/0027534 | A1 | 2/2007 | Bergheim et al. |
| 2007/0043435 | A1 | 2/2007 | Seguin et al. |
| 2007/0055358 | A1 | 3/2007 | Krolik et al. |
| 2007/0067029 | A1 | 3/2007 | Gabbay |
| 2007/0093890 | A1 | 4/2007 | Eliasen et al. |
| 2007/0100435 | A1 | 5/2007 | Case et al. |
| 2007/0118210 | A1 | 5/2007 | Pinchuk |
| 2007/0198097 | A1 | 8/2007 | Zegdi |
| 2007/0213813 | A1 | 9/2007 | Von Segesser et al. |
| 2007/0233228 | A1 | 10/2007 | Eberhardt et al. |
| 2007/0244545 | A1 | 10/2007 | Birdsall et al. |
| 2007/0244552 | A1 | 10/2007 | Salahieh et al. |
| 2007/0288087 | A1 | 12/2007 | Fearnot et al. |
| 2008/0021552 | A1 | 1/2008 | Gabbay |
| 2008/0039934 | A1 | 2/2008 | Styrc |
| 2008/0071369 | A1 | 3/2008 | Tuval et al. |
| 2008/0082164 | A1 | 4/2008 | Friedman |
| 2008/0097595 | A1 | 4/2008 | Gabbay |
| 2008/0114452 | A1 | 5/2008 | Gabbay |
| 2008/0125853 | A1 | 5/2008 | Bailey et al. |
| 2008/0140189 | A1 | 6/2008 | Nguyen et al. |
| 2008/0147183 | A1 | 6/2008 | Styrc |
| 2008/0154355 | A1 | 6/2008 | Benichou et al. |
| 2008/0154356 | A1 | 6/2008 | Obermiller et al. |
| 2008/0243245 | A1 | 10/2008 | Thambar et al. |
| 2008/0255662 | A1 | 10/2008 | Stacchino et al. |
| 2008/0262602 | A1 | 10/2008 | Wilk et al. |
| 2008/0269879 | A1 | 10/2008 | Sathe et al. |
| 2009/0099653 | A1 | 4/2009 | Suri et al. |
| 2009/0112309 | A1 | 4/2009 | Jaramillo et al. |
| 2009/0138079 | A1 | 5/2009 | Tuval et al. |
| 2010/0004740 | A1 | 1/2010 | Seguin et al. |
| 2010/0036484 | A1 | 2/2010 | Hariton et al. |
| 2010/0049306 | A1 | 2/2010 | House et al. |
| 2010/0087907 | A1 | 4/2010 | Lattouf |
| 2010/0131055 | A1 | 5/2010 | Case et al. |
| 2010/0168778 | A1 | 7/2010 | Braido |
| 2010/0168839 | A1 | 7/2010 | Braido et al. |
| 2010/0185277 | A1 | 7/2010 | Braido et al. |
| 2010/0191326 | A1 | 7/2010 | Alkhatib |
| 2010/0204781 | A1 | 8/2010 | Alkhatib |
| 2010/0204785 | A1 | 8/2010 | Alkhatib |
| 2010/0217382 | A1 | 8/2010 | Chau et al. |
| 2010/0249911 | A1 | 9/2010 | Alkhatib |
| 2010/0249923 | A1 | 9/2010 | Alkhatib et al. |
| 2010/0286768 | A1 | 11/2010 | Alkhatib |
| 2010/0298931 | A1 | 11/2010 | Quadri et al. |
| 2011/0029072 | A1 | 2/2011 | Gabbay |
| 2012/0303116 | A1 | 11/2012 | Gorman, III et al. |
| 2014/0005776 | A1 * | 1/2014 | Braido ............... A61F 2/2418 623/2.18 |

(56) References Cited

U.S. PATENT DOCUMENTS

| | | | |
|---|---|---|---|
| 2019/0091014 A1 | 3/2019 | Arcaro et al. | |
| 2021/0259833 A1* | 8/2021 | Maimon | A61F 2/2412 |

FOREIGN PATENT DOCUMENTS

| | | | |
|---|---|---|---|
| DE | 102005003632 A1 | 8/2006 | |
| DE | 202008009610 U1 | 12/2008 | |
| EP | 0850607 A1 | 7/1998 | |
| EP | 1000590 A1 | 5/2000 | |
| EP | 1360942 A1 | 11/2003 | |
| EP | 1584306 A1 | 10/2005 | |
| EP | 1598031 A2 | 11/2005 | |
| EP | 1926455 A2 | 6/2008 | |
| FR | 2850008 A1 | 7/2004 | |
| FR | 2847800 B1 | 10/2005 | |
| WO | 9930646 A1 | 6/1999 | |
| WO | 02067782 A2 | 9/2002 | |
| WO | 2005070343 A1 | 8/2005 | |
| WO | 07071436 A2 | 6/2007 | |
| WO | 08070797 A2 | 6/2008 | |

OTHER PUBLICATIONS

Ruiz, Carlos, Overview of PRE-CE Mark Transcatheter Aortic Valve Technologies, Euro PCR—dated May 25, 2010.

"Percutaneous Aortic Valve Replacement: Resection Before Implantation", Quaden, Rene et al., European J. of Cardio-Thoracic Surgery, vol. 27, No. 5, May 2005, pp. 836-840.

Braido, et al., U.S. Appl. No. 29/375,243, filed Sep. 20, 2010, titled "Surgical Stent Assembly".

"Catheter-Implanted Prosthetic Heart Valves: Transluminal Catheter Implantation of a New Expandable Artificial Heart Valve in the Descending Thoracic Aorta in Isolated Vessels and Closed Chest Pigs", Knudsen et al., The International Journal of Artificial Organs, vol. 16, No. 5, May 1993, pp. 253-262.

"Transluminal Aortic Valve Placement. A Feasability Study with a Newly Designed Collapsible Aortic Valve", Moazami et al., ASAIO Journal, vol. 42, No. 5, 1996, pp. M381-M385.

"Transluminal Catheter Implanted Prosthetic Heart Valves", Andersen, H. R., International Journal of Angiology, vol. 7, No. 2, Mar. 1998, pp. 102-106.

"Transluminal Implantation of Artificial Heart Valves", Andersen, H. R., et al., European Heart Journal, vol. 13, No. 5, May 1992, pp. 704-708.

Is It Reasonable to Treat All Calcified Stenotic Aortic Valves With a Valved Stent?, 579-584, Zegdi, Rachid, MD, PhD et al., J. of the American College of Cardiology, vol. 51, No. 5, Feb. 5, 2008.

"Direct-Access Valve Replacement", Christoph H. Huber, et al., Journal of the American College of Cardiology, vol. 46, No. 2, (Jul. 19, 2005).

"Percutaneous Aortic Valve Implantation Retrograde From the Femoral Artery", John G. Webb et al., Circulation, 2006; 113:842-850 (Feb. 6, 2006).

"Minimally invasive cardiac surgery", M. J. Mack, Surgical Endoscopy, 2006, 20:S488-S492, DOI: 10.1007/s00464-006-0110-8 (presented Mar. 23, 2006).

"Transapical Transcatheter Aortic Valve Implantation in Humans", Samuel V. Lichtenstein et al., Circulation. 2006; 114: 591-596 (Jul. 31, 2006).

"Closed Heart Surgery: Back to the Future", Samuel V. Lichtenstein, The Journal of Thoracic and Cardiovascular Surgery, vol. 131, No. 5, May 2006, pp. 941-943.

"Transapical Approach for Sutureless Stent-Fixed Aortic Valve Implantation: Experimental Results", Th. Walther et al., European Journal of Cardio-Thoracic Surgery, vol. 29, No. 5, May 2006, pp. 703-708.

"Transapical aortic valve implantation: an animal feasibility study"; Todd M. Dewey et al., The annals of thoracic surgery 2006; 82: 110-6 (Feb. 13, 2006).

Transcatheter Valve Repair, Hijazi et al., CRC Press, Jan. 2006, pp. 165-186.

* cited by examiner

ALTERNATE STENT CAF DESIGN FOR TAVR

CROSS-REFERENCE TO RELATED APPLICATIONS

The present application claims the benefit of U.S. Provisional Application Ser. No. 62/880,758, filed Jul. 31, 2019, entitled Alternate Stent CAP Design for TAVR, the disclosure of which is hereby incorporated herein by reference.

BACKGROUND OF THE INVENTION

The present invention relates to collapsible prosthetic heart valves, and more particularly, to prosthetic heart valves having commissure attachment features that reduce strain on the leaflets of the prosthetic valve and methods of manufacturing the commissure attachment features.

Diseased and/or defective heart valves may lead to serious health complications. One method of addressing this condition is to replace a non-functioning heart valve with a prosthetic valve. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed to reduce its circumferential size.

When a collapsed prosthetic valve has reached the desired implant site in the patient (e.g., at or near the annulus of the patient's heart valve that is to be repaired by the prosthetic valve), the prosthetic valve can be deployed or released from the delivery apparatus and expanded to its full operating size. For balloon-expandable valves, this generally involves releasing the entire valve, assuring its proper location and then expanding a balloon positioned within the valve stent. For self-expanding valves, on the other hand, the stent automatically expands as the stent is withdrawn from the delivery apparatus.

Properly functioning prosthetic heart valves maintain unidirectional blood flow in the circulatory system by opening and closing, depending on the difference in the pressure on opposite sides of the valve. Prosthetic aortic heart valves prevent backflow from the aorta into the left ventricle during systole.

Despite the improvements that have been made to prosthetic heart valves, various shortcomings remain. For example, prosthetic heart valves have limited life expectancies for a variety of reasons. Thrombus buildup, for example, may prevent the prosthetic leaflets from properly coapting. Moreover, the prosthetic heart valve may be susceptible to failure at high stress regions, such as the leaflet commissure attachment feature, causing the prosthetic leaflets to tear and/or the sutures that attach the prosthetic valve assembly to the stent to tear.

Therefore, there is a need for improvements to the commissure attachment features of prosthetic heart valves that adequately secure the prosthetic leaflets to the stent in a manner that reduces the strain placed on the valve assembly without affecting the prosthetic heart valve's ability to collapse.

BRIEF SUMMARY OF THE INVENTION

In accordance with a first aspect of the present invention, a commissure attachment feature extends in a medial direction of a stent for coupling a valve assembly to the stent. Among other advantages, this attachment feature permits adjacent leaflets to be sutured to one another to improve blood washout of the neo-sinus of the prosthetic heart valve to prevent the formation of thrombus, and to redistribute strain from the commissure of the leaflets to the stent. Redistributing the strain in this manner reduces the likelihood that the prosthetic leaflets will tear.

One embodiment of the device includes a stent extending in a longitudinal direction and having a collapsed condition and an expanded condition. The stent includes a plurality of struts forming cells and a plurality of commissure attachment features spaced apart in an annular direction of the stent. Each of the commissure attachment features is attached to select ones of the struts and extends in a medial direction of the stent. A valve assembly is secured to the plurality of commissure attachment features, the valve assembly including a cuff and a plurality of leaflets, each of the leaflets having a free edge and being capable of alternating between an open position and a closed position.

A method of manufacturing a prosthetic heart valve is also provided. The method includes cutting a tubular material to form a stent, the stent extending in a longitudinal direction and having a collapsed condition and an expanded condition. The stent includes a plurality of struts forming cells and a plurality of commissure attachment features spaced apart in an annular direction of the stent. The method further includes bending each of the commissure attachment features from a first orientation to a second orientation different from the first orientation, and coupling a valve assembly to the commissure attachment features, the valve assembly including a cuff and a plurality of leaflets, each of the leaflets having a free edge and being capable of alternating between an open position and a closed position.

BRIEF DESCRIPTION OF THE DRAWINGS

Various embodiments of the present invention are described herein with reference to the drawings, wherein.

DETAILED DESCRIPTION

As used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. As used herein, the terms "generally," "substantially," "approximately" and "about" are intended to mean that slight deviations from absolute are included within the scope of the term so modified.

Figure 1:
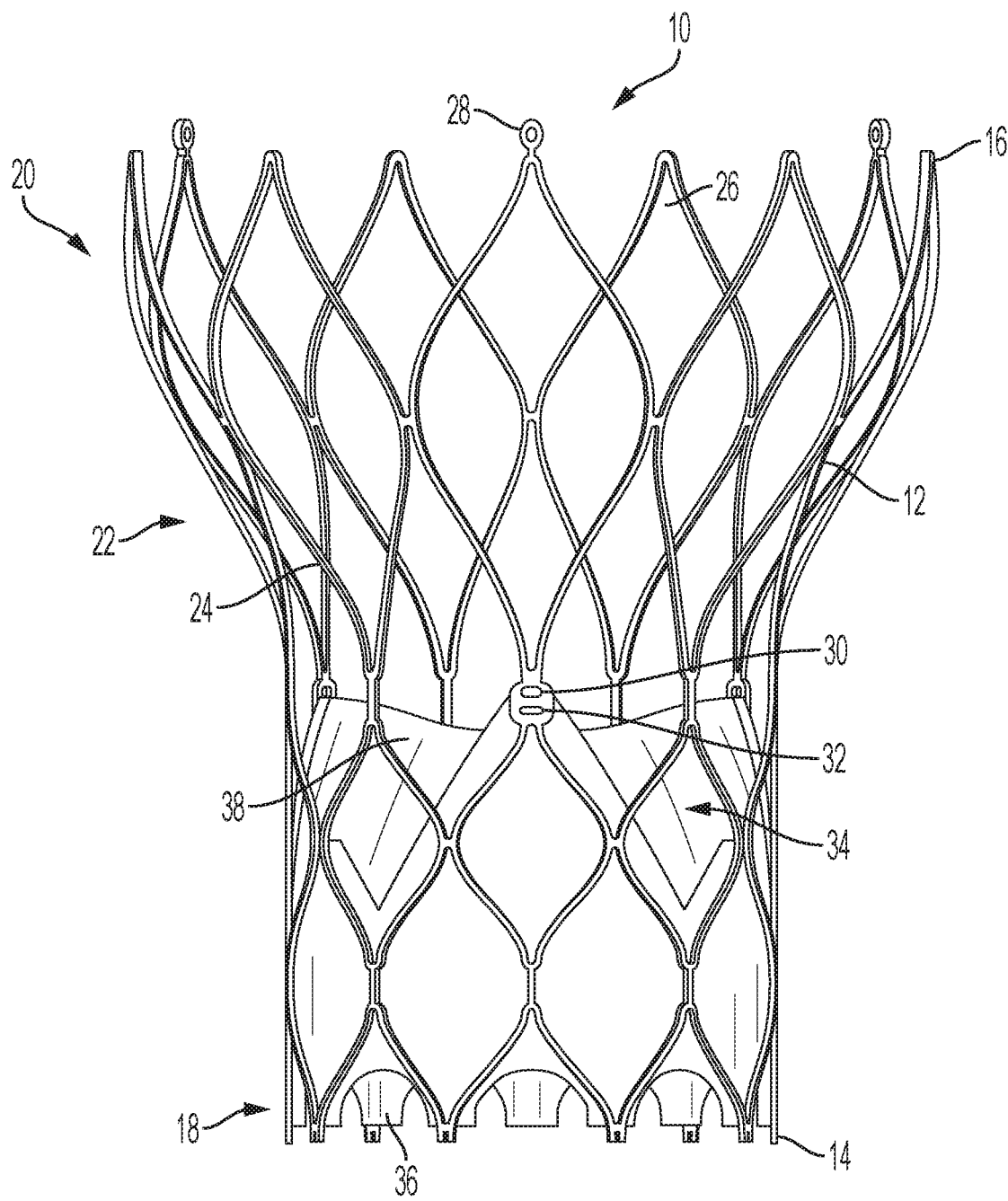
FIG. 1 is a side elevational view of a collapsible prosthetic heart valve in accordance with the prior art.

FIG. 1 illustrates a collapsible prosthetic heart valve 10 that is designed to replace the function of the native aortic valve of a patient. Prosthetic heart valve 10 includes an expandable stent 12 which may be formed from biocompatible materials that are capable of self-expansion, for example, shape memory alloys such as nitinol. Stent 12 extends from a proximal or annulus end 14 to a distal or aortic end 16, and includes an annulus section 18 adjacent the proximal end and an aortic section 20 adjacent the distal end. Annulus section 18 has a relatively small cross-section in an expanded condition compared to aortic section 20 in the expanded condition. Annulus section 18 may be in the form of a cylinder having a substantially constant diameter along its length. A transition section 22 tapers outwardly from annulus section 18 to aortic section 20. Each of the sections of stent 12 includes a plurality of struts 24 which form a plurality of cells 26 that are connected to one another in one or more annular rows around the stent. Annulus section 18 may have two annular rows of complete cells and aortic section 20 and transition section 22 may each have one or more annular rows of partial cells. The cells in aortic section 20 may be larger than the cells in annulus section 18. The larger cells in aortic section 20 facilitate positioning prosthetic valve 10 within the native aortic annulus such that stent 12 does not interfere with blood flow to the coronary arteries.

Stent 12 includes one or more retaining elements 28 at distal end 16. Retaining elements 28 are sized to cooperate with a corresponding retaining structure on a delivery device. This cooperation minimizes axial movement of the prosthetic heart valve relative to the delivery device during unsheathing or resheathing procedures, and prevents rotation of the prosthetic heart valve relative to the delivery device as the delivery device is advanced to the target location and during deployment.

Stent 12 may also include a plurality of commissure attachment features 30 for attaching the commissure between two adjacent leaflets to the stent. As shown in FIG. 1, commissure attachments features 30 are disposed within the wall of stent 12 and may lie at the intersection of four cells 26, two of the cells being adjacent to one another in the same annular row, and the other two cells being in different annular rows and lying in end-to-end relationship. Commissure attachment features 30 are preferably positioned entirely within annulus section 18, or at the juncture of the annulus section and transition section 22. Commissure attachment features 30 may include one or more eyelets 32 which facilitate the suturing of the leaflet commissure to stent 12.

Prosthetic heart valve 10 also includes a valve assembly 34, which may be positioned entirely within annulus section 18 and secured to stent 12 by suturing the valve assembly to struts 24 and/or to commissure attachment features 30. That is, the entire valve assembly 34 may be axially positioned between the proximal end 14 of stent 12 and commissure attachment features 30, such that none of the valve assembly is positioned between the commissure attachment features and the distal end 16 of the stent. Valve assembly 34 includes a cuff 36 and a plurality of leaflets 38 which open and close collectively to function as a one-way valve. Both cuff 36 and leaflets 38 may be wholly or partly formed of any suitable biological material, such as bovine or porcine pericardium, or biocompatible polymers, such as PTFE, urethanes and the like.

Prosthetic heart valve 10 may be used to replace a native valve, a surgical heart valve or a heart valve that has undergone a surgical procedure. Prosthetic heart valve 10 may be delivered to the desired site (e.g., near the native aortic annulus) using any suitable delivery device. During delivery, prosthetic heart valve 10 is disposed inside the delivery device in a collapsed condition. The delivery device may be introduced into a patient using a transfemoral, transapical, transseptal or any other percutaneous approach. Once the delivery device has reached the target site, the user may deploy prosthetic heart valve 10. Upon deployment, prosthetic heart valve 10 expands so that the annulus section 18 of stent 12 is in secure engagement within the native annulus.

Figure 2:
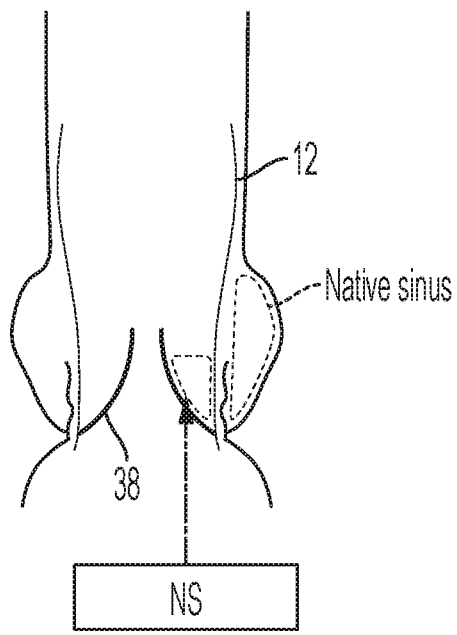
FIG. 2 is a highly schematic cutaway view of the prosthetic heart valve of FIG. 1 disposed within the aortic valve annulus of patient.

FIG. 2 is a highly schematic cutaway view showing prosthetic heart valve 10 disposed within the native aortic annulus of a patient. When prosthetic heart valve 10 is properly positioned within the native annulus, it works as a one-way valve, allowing blood to flow from the left ventricle of the heart to the aorta during systole, and preventing blood from flowing in the opposite direction. Long term clinical success, and ultimately the life of prosthetic heart valve 10 is dependent, in part, on the ability of the free edges of leaflets 38 to properly coapt. Thrombus buildup in the neo-sinus NS of prosthetic heart valve 10 may restrict motion of leaflets 38 and prevent the leaflets from coapting.

Figure 3:
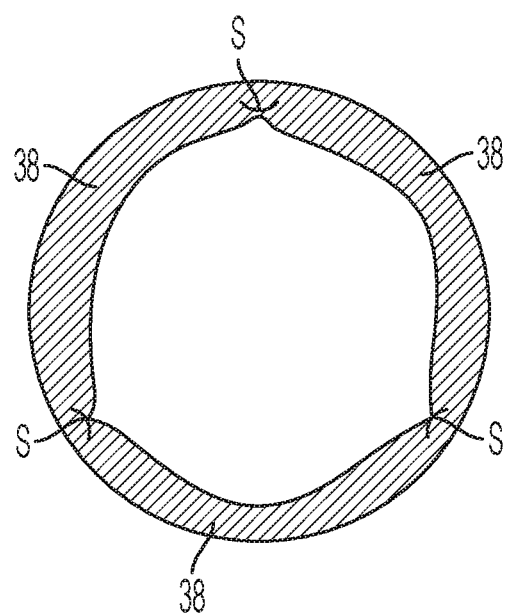
FIG. 3 is a highly schematic top view of the prosthetic heart valve of FIG. 1 showing the commissure of adjacent leaflets sutured together.

Suturing the commissures of leaflets 38 radially inward of the commissure attachments features 30 of stent 12, as shown in FIG. 3, reduces the cross-sectional area of the lumen of prosthetic heart valve 10, and results in increased velocity of blood flow through the neo-sinus during systole. The increased blood flow velocity is believed to improve blood wash out from the neo-sinus and reduce thrombus build up. However, the addition of sutures S places additional strain on the leaflets 38 of valve assembly 34 and increases the likelihood that the valve assembly will fail at this junction. Failure may, for example, include tearing of sutures S and/or the leaflets 38 of valve assembly 34.

Figure 4:
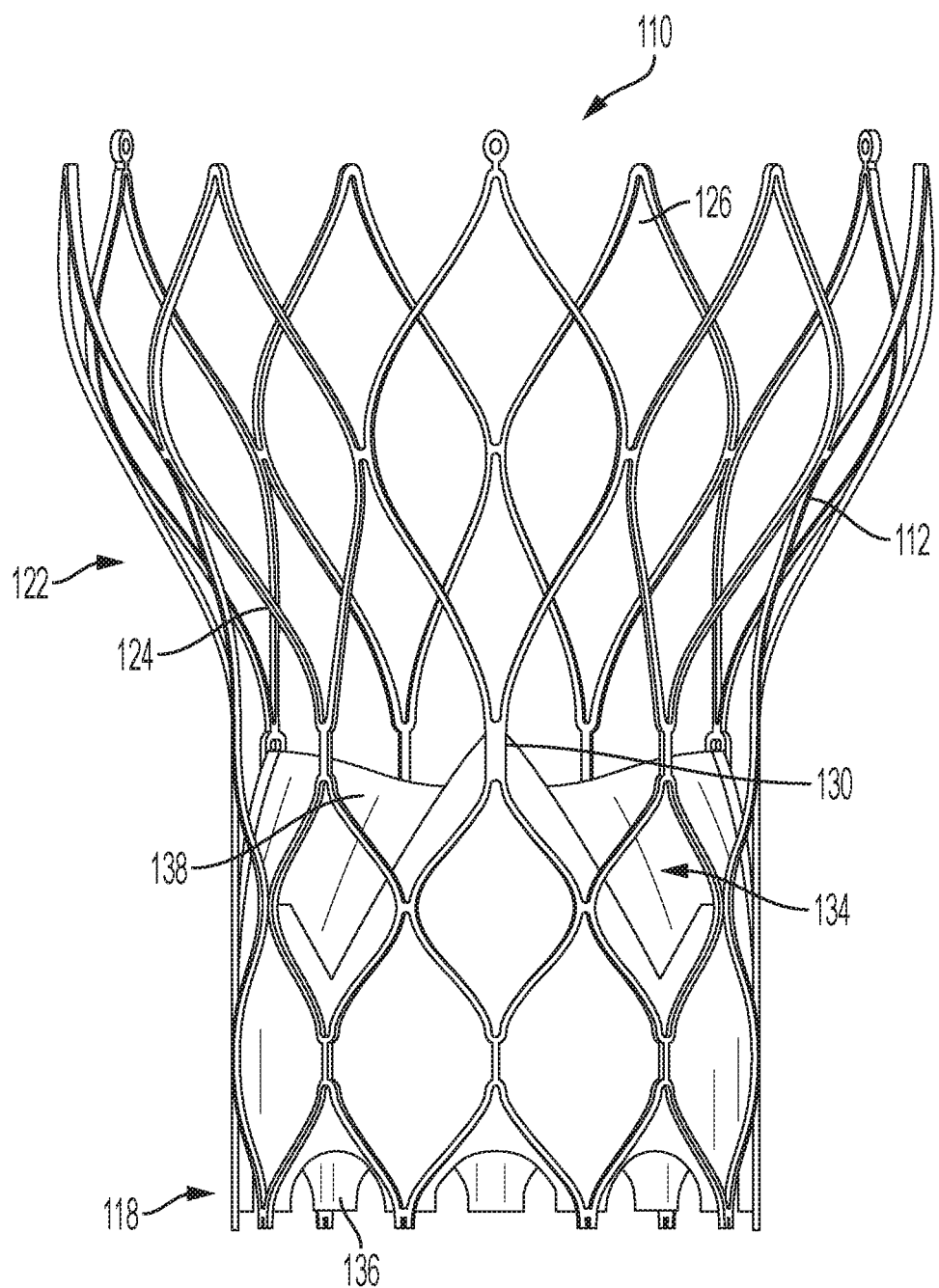
FIG. 4 is a side elevational view of a collapsible prosthetic heart valve in accordance with an embodiment of the present invention.

FIG. 4 illustrates a prosthetic heart valve 110 according to an embodiment of the present invention. Prosthetic heart valve 110 includes all of the features of prosthetic heart valve 10, except for commissure attachment features 30. Accordingly, each of the features of prosthetic heart valve 110 that correspond to features of prosthetic heart valve 10 are not described again hereinafter. Instead, when such features are referenced or illustrated in FIGS. 4-7, these features are described and illustrated using corresponding 100 series numerals.

Figure 5:
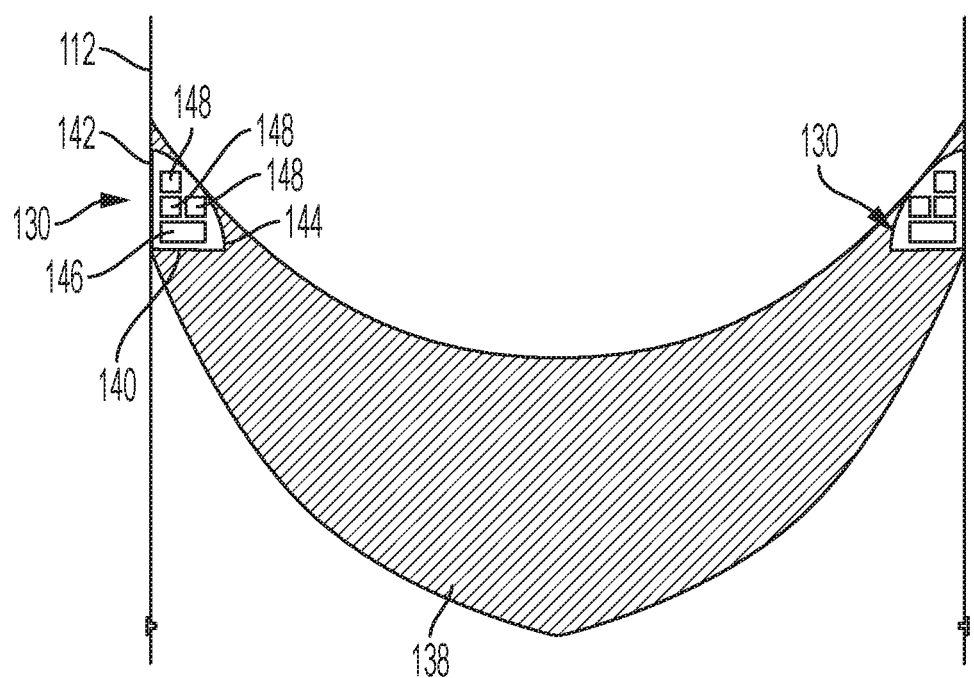
FIG. 5 is a highly schematic cross-sectional view of the prosthetic heart valve of FIG. 4 showing a commissure attachment feature in accordance with an embodiment of the present invention.

Prosthetic heart valve 110 replaces commissure attachment features 30 with commissure attachment features 130, shown in FIG. 5. Commissure attachment features 130 are designed to redistribute strain from the leaflets 138 of prosthetic heart valve 110 to the stent 112 of the prosthetic heart valve. Commissure attachment features 130 are spaced apart from one another in an annular direction of stent 112 and disposed within a predetermined one of the annular rows of cells 126. Preferably, commissure attachment features 130 are disposed in one of the rows of cells within the annulus section 118 of stent 112, or in one of the rows of cells at the juncture of the annulus section and the transition section 122 of the stent. Since FIG. 4 illustrates a prosthetic heart valve 110 for replacing a native tricuspid valve, such as the aortic valve, prosthetic heart valve 110 is illustrated with three leaflets 138, as well as three commissure attachment features 130. However, it will be appreciated that prosthetic heart valves according to this aspect of the invention may have a greater or lesser number of leaflets 138 and/or commissure attachment features 130. For example, if prosthetic heart valve 110 were a prosthetic heart valve for replacing a native bicuspid valve, such as a mitral valve, the prosthetic heart valve may include two commissure attachment features 130 for attaching each of the two prosthetic leaflets 138 to stent 112.

Referring to FIG. 5, each one of the plurality of commissure attachment features 130 includes a body 140 that has a length in a longitudinal direction of stent 112, a width in a radial direction of the stent and a thickness (not shown) in an annular direction of the stent, the width being greater than the thickness. The width of body 140 may be about 3.0 mm or less, and is preferably between about 2.0 mm and about 2.5 mm. Commissure attachment features 130 may be positioned above the bulk of leaflets 138. In light of this and that the commissure attachment features have a relatively small dimension in the medial direction of stent 112, the collapsibility of prosthetic heart valve 110 is not inhibited. Accordingly, prosthetic heart valve 110 can be collapsed into a competitive French delivery system, for example, an 18 French delivery device.

The body 140 of commissure attachment feature 130 has a side 142 that is attached to select struts 124 of stent 112, and a free edge 144 that is disposed in an interior region the stent. That is, the body 140 of commissure attachment feature 130 extends from select struts 124 in a medial direction of stent 112 (i.e., toward the middle of the stent or radially inward). In other words, body 140 extends orthogonal to the annular direction of stent 112 toward the center of the stent. The body 140 of commissure attachment feature 130 may be shaped as a quarter ellipse, or a quarter circle, such that the free edge 144 of the body forms an arc extending from a distal end of the attached side 142 of the body to a proximal end of the free edge spaced radially inward from stent 112.

The body 140 of commissure attachment feature 130 may include a plurality of apertures or eyelets for connecting valve assembly 134 to stent 112. Thus, body 140 may include an eyelet 146 for coupling cuff 136 to stent 112, and one or more smaller eyelets 148 for suturing adjacent leaflets 138 to one another and to the commissure attachment feature. At least one of leaflet attachment eyelets 148 may be spaced from the attached side 142 of commissure attachment feature 130 so as to be spaced from a luminal surface of stent 112.

Figure 6:
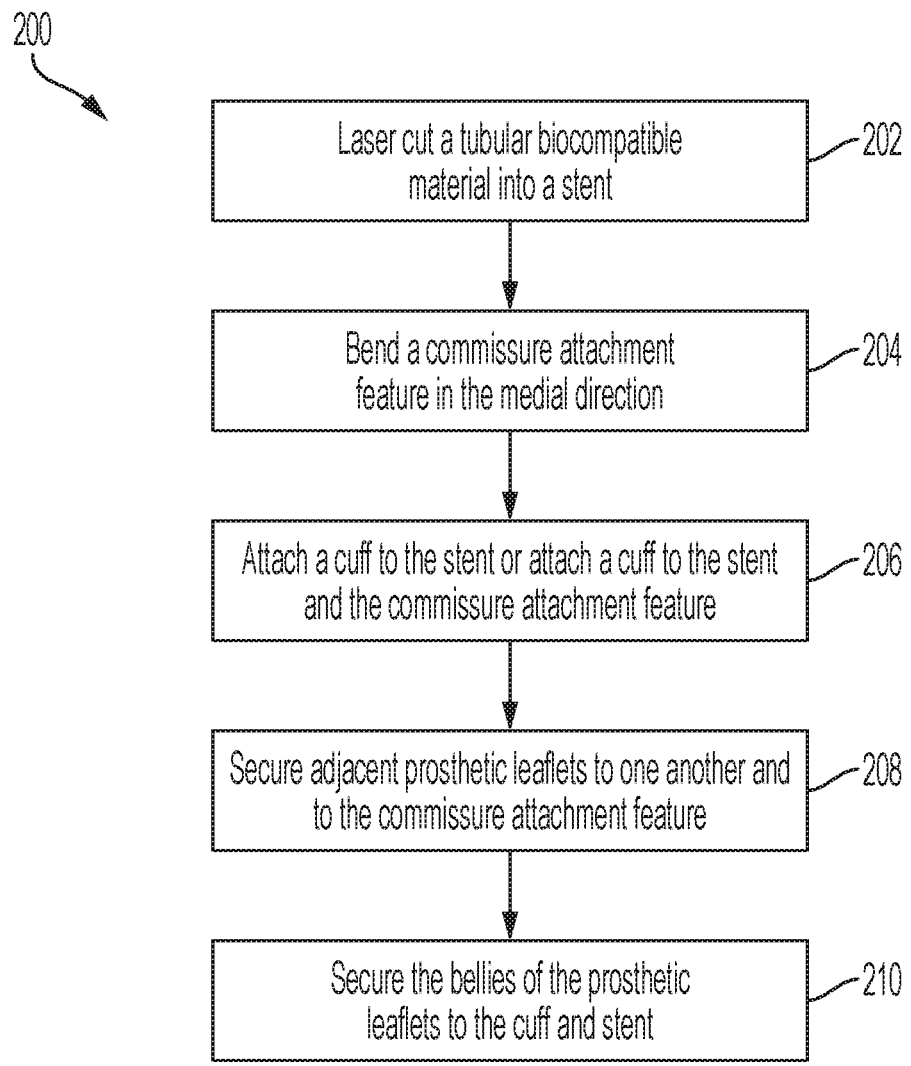
FIG. 6 is a flow chart showing a method of manufacturing the prosthetic heart valve of FIG. 4.
Figure 7:
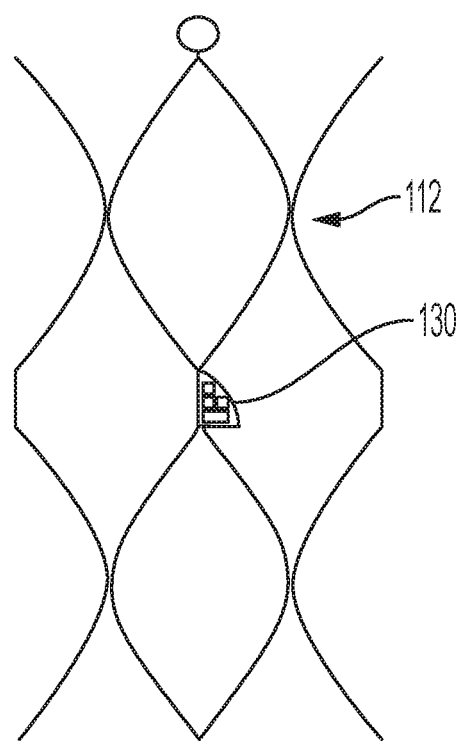
FIG. 7 is a highly schematic fragmentary view of the stent of the prosthetic heart valve of FIG. 4.

FIG. 6 is a flow chart depicting a method 200 of manufacturing prosthetic heart valve 110. In a first step 202, a tube of nitinol is placed around a mandrel and cut, preferably by a laser or other technique, to form stent 112. A fragmentary view of stent 112 after the tube has been cut and radially expanded is illustrated in FIG. 7. As shown, commissure attachment features 130 initially extend in a lateral direction relative to the struts 124 of stent 112. That is, commissure attachment features 130 initially lie within the circumference of stent 112. In a next step 204, the user may bend commissure attachment features 130 from their initial positions (e.g., the lateral or circumferential direction) to final positions (e.g., the medial or radial direction) as shown in FIG. 5. Commissure attachment features 130 are then heat set, or otherwise permanently set, in this position.

After commissure attachment features 130 are set in their final positions, cuff 136 may be attached to stent 112 in step 206, for example, by suturing the cuff to the stent. Although not required, a suture may additionally be pierced through cuff 136 and passed through the cuff attachment eyelet 146 of commissure attachment feature 130 before the suture is again pierced through the cuff. This additional step may optionally be repeated for each one of commissure attachment features 130. The ends of adjacent leaflets may then be sutured together and coupled to the commissure attachment feature 130. In this step 208, a suture may pierce through a first one of the leaflets, pass through at least one of the leaflet attachment eyelets 148 of commissure attachment feature 130, and then pierce through an adjacent leaflet. In a final step 210, the belly of each one of leaflets 138 may then be sutured to cuff 136 and stent 112. In an exemplary embodiment, a series of suture loops extend along the belly of each one of the leaflets in a parabolic shape, and further secure the leaflets to the stent.

By connecting the leaflet commissures to commissure attachment feature 130 at a position spaced medially inward from stent 112, the cross-sectional area of the lumen of prosthetic heart valve 110 is reduced, such that the velocity of blood flow through the lumen during systole will be increased. As a result of the increased blood flow velocity, some of the blood will form an eddy in the neo-sinus, and wash out from the neo-sinus is improved and thrombus build up is reduced. Moreover, because adjacent leaflets are sutured together via medially extending commissure attachment features 130, when a stress is applied to the prosthetic valve leaflets 138, the stress is transferred away from the prosthetic leaflets to the commissure attachment features and stent 112. This reduces the likelihood that valve assembly 134 will fail under stress and prolongs the life of prosthetic heart valve 110.

To summarize the foregoing, a prosthetic heart valve, includes a stent extending in a longitudinal direction and having a collapsed condition and an expanded condition, the stent including a plurality of struts forming cells and a plurality of commissure attachment features spaced apart in an annular direction of the stent, each of the commissure attachment features being attached to select ones of the struts and extending in a medial direction of the stent; and a valve assembly secured to the plurality of the commissure attachment features, the valve assembly including a cuff and a plurality of leaflets, each of the leaflets having a free edge and being capable of alternating between an open position and a closed position; and/or each of the commissure attachment features may extend substantially orthogonal to the annular direction of the stent; and/or the stent and the commissure attachment features may be integrally formed; and/or the stent and the commissure attachment features may be formed of nitinol; and/or each one of the commissure attachment features may be located in the annulus section of the stent and/or a width of the commissure attachment feature in the medial direction is about 3.0 mm or less; and/or a width of the commissure attachment feature in the medial direction may be between about 2.0 mm and about 2.5 mm; and/or the commissure attachment feature may include an eyelet; and/or the eyelet may be spaced in the medial direction from a luminal surface of the stent; and/or the cuff may be disposed on a luminal surface of the stent; and/or two of the leaflets may be sutured to each of the commissure attachment features; and/or each of the commissure attachment features may have a side attached to the stent and an arcuate edge extending between a distal end of the side and a proximal end of the arcuate edge spaced in the medial direction from the stent; and/or the stent may include three of the commissure attachment features; and/or the cells may be connected to one another in a plurality of annular rows about the stent, each one of the plurality of commissure attachment features being disposed in a predetermined one of the annular rows.

A method of manufacturing a prosthetic heart valve is also provided. The method includes cutting a tubular material to form a stent, the stent extending in a longitudinal direction and having a collapsed condition and an expanded condition, the stent including a plurality of struts forming cells and a plurality of commissure attachment features spaced apart in an annular direction of the stent; bending each of the commissure attachment features from a first orientation to a second orientation different from the first orientation; and coupling a valve assembly to the commissure attachment features, the valve assembly including a cuff and a plurality of leaflets, each of the leaflets having a free edge and being capable of alternating between an open position and a closed position; and/or the first orientation may be an annular direction of the stent and the second orientation may be a medial direction of the stent; and/or the coupling step may comprise suturing each commissure formed by adjacent ones of the leaflets to a respective one of the commissure attachment features; and/or the method may further comprise suturing a belly of each one of the leaflets to the cuff and the stent; and/or the tubular material may be nitinol; and/or the method may further comprise heat setting the nitinol after the bending step.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic heart valve, comprising:
an expandable stent extending in a longitudinal direction and having an annulus section and an aortic section, the stent including a plurality of struts forming cells and a plurality of commissure attachment features spaced apart from one another in an annular direction of the stent, each of the commissure attachment features being attached to select ones of the struts in the annulus section and having a length in the longitudinal direction, a thickness in the annular direction, and a width extending from the select ones of the struts in a radial direction of the stent toward a longitudinal axis of the stent, the width being greater than the thickness; and
a valve assembly secured to the plurality of the commissure attachment features, the valve assembly including a cuff and a plurality of leaflets, each of the leaflets having a free edge and being capable of alternating between an open position and a closed position.

2. The valve of claim 1, wherein the stent and the commissure attachment features are integrally formed.

3. The valve of claim 1, wherein the stent and the commissure attachment features are formed of nitinol.

4. The valve of claim 1, wherein the width of each of the commissure attachment features in the radial direction is about 3.0 mm or less.

5. The valve of claim 1, wherein the width of each of the commissure attachment features in the radial direction is between about 2.0 mm and about 2.5 mm.

6. The valve of claim 1, wherein each of the commissure attachment features includes an eyelet.

7. The valve of claim 6, wherein the eyelet is spaced in the radial direction from a luminal surface of the stent.

8. The valve of claim 1, wherein the cuff is disposed on a luminal surface of the stent.

9. The valve of claim 1, wherein two of the leaflets are sutured to each of the commissure attachment features.

10. The valve of claim 1, wherein each of the commissure attachment features has a side attached to the stent and an arcuate edge extending between a distal end of the side and a proximal end of the arcuate edge spaced in the radial direction from the stent.

11. The valve of claim 1, wherein the stent includes three of the commissure attachment features.

12. The valve of claim 1, wherein the cells are connected to one another in a plurality of annular rows about the stent, each of the commissure attachment features being disposed in a predetermined one of the annular rows.

13. A prosthetic heart valve, comprising:
an expandable stent extending in a longitudinal direction, the stent including a plurality of struts forming cells and a plurality of commissure attachment features spaced apart in an annular direction of the stent, each of the commissure attachment features being attached to select ones of the struts and having opposing major surfaces defining an eyelet therethrough, the opposing major surfaces each having a width extending in a radial direction of the stent so as to extend from the select ones of the struts toward a longitudinal axis of the stent, and the opposing major surfaces being separated by a thickness extending in the annular direction of the stent, the width being grater than the thickness; and
a valve assembly secured to the plurality of the commissure attachment features, the valve assembly including a cuff and a plurality of leaflets, each of the leaflets having a free edge and being capable of alternating between an open position and a closed position.

* * * * *